(12) United States Patent
Sigl et al.

(10) Patent No.: US 7,074,964 B2
(45) Date of Patent: Jul. 11, 2006

(54) PREPARATION OF ALKYLAMINES AND METHOD OF INCREASING THE HYDROAMINATION ACTIVITY OF CALCINED ZEOLITIC CATALYSTS

(75) Inventors: Marcus Sigl, Mannheim (DE); Ulrich Müller, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 57 days.

(21) Appl. No.: 10/806,248

(22) Filed: Mar. 23, 2004

(65) Prior Publication Data

US 2004/0192970 A1 Sep. 30, 2004

(30) Foreign Application Priority Data

Mar. 27, 2003 (DE) ................................ 103 13 853

(51) Int. Cl.
*C07C 209/60* (2006.01)

(52) U.S. Cl. ...................................... 564/485; 564/408
(58) Field of Classification Search ...................... None
See application file for complete search history.

(56) References Cited

U.S. PATENT DOCUMENTS

| | | | |
|---|---|---|---|
| 5,174,976 A * | 12/1992 | Chu et al. ................ | 423/328.2 |
| 6,143,934 A | 11/2000 | Dingerdissen et al. | |
| 6,576,796 B1 | 6/2003 | Funke et al. | |

FOREIGN PATENT DOCUMENTS

| | | |
|---|---|---|
| CA | 1216596 | 1/1987 |
| EP | 133 938 | 3/1985 |
| EP | 263 462 | 4/1988 |
| WO | 97/07088 | 2/1997 |
| WO | 02/00597 | 1/2002 |

OTHER PUBLICATIONS

Derwent Abst. 87-199721/29 (1986).

* cited by examiner

*Primary Examiner*—Brian Davis
(74) *Attorney, Agent, or Firm*—Novak Druce & Quigg, LLP; Jason D. Voight

(57) ABSTRACT

In a process for preparing alkylamines by reacting olefins with ammonia, primary or secondary amines under hydroaminating conditions over a calcined zeolitic catalyst, the calcined zeolitic catalyst is thermally activated at from 100 to 550° C. in a gaseous stream of air, nitrogen, other inert gases or mixtures thereof not more than 24 hours before commencement of the reaction.

13 Claims, No Drawings

PREPARATION OF ALKYLAMINES AND METHOD OF INCREASING THE HYDROAMINATION ACTIVITY OF CALCINED ZEOLITIC CATALYSTS

The present invention relates to a process for preparing alkylamines by reacting olefins with ammonia, primary or secondary amines under hydroaminating conditions over a calcined zeolitic catalyst. The invention further relates to a method of increasing the hydroamination activity of calcined zeolitic catalysts and to the catalysts obtained in this way.

The use of zeolites as catalysts for the amination of olefins by means of ammonia or primary or secondary amines has been known for a relatively long time. Thus, EP-A 0 133 938 describes a process for preparing amines from olefins and ammonia, primary, secondary amines or mixtures thereof in the presence of a borosilicate or borogermanate zeolite of the pentasil type as catalyst. The amines obtained are separated off from the reaction mixture and unreacted starting materials are recirculated.

The patent application states that after the zeolitic catalysts have been deactivated by deposition of carbon during the reaction, they can be regenerated in a simple manner by burning off the coke deposits using air or an air/nitrogen mixture at from 400 to 500° C., preferably at about 500° C. It is stated that the initial activity of the catalysts is restored as a result. An increase in activity of catalysts which have not been deactivated in this way is not described.

EP-A 0 263 462 likewise relates to a process for preparing amines from olefins and ammonia, primary or secondary amines in the presence of a chromium-containing borosilicate zeolite or chromium-containing iron silicate zeolite of the pentasil type as catalyst. It is stated that calcined iron silicate and borosilicate zeolites can be doped with chromium by impregnating them with a solution of a chromium compound. The impregnation is followed by drying, after which repeated calcination can be carried out. It is also stated that after-treatment of the doped zeolites with hydrogen can be advantageous. Furthermore, mention is once again made of the restoration of the initial activity of catalysts which have been deactivated by deposition of carbon.

WO 02/00597 relates to a process for preparing alkylamines in which an olefin is reacted with ammonia, a primary amine and/or a secondary amine under hydroaminating conditions in a first process step and the hydroamination product or products obtained is/are reacted under transalkylating conditions in a second process step.

It is indicated that zeolitic catalysts in particular can be used in the reaction. It is also indicated that these acid catalysts also comprise previously used material or can consist of such material which has been regenerated by customary methods, for example by recalcination in air, water, carbon dioxide or inert gas at >200° C. by washing with water, acids or organic solvents, by steaming or by treatment at above 200° C. under reduced pressure.

WO 97/07088 relates to a process for preparing amines by reacting olefins with ammonia, primary or secondary amines in the presence of a zeolitic catalyst. In this process, a boron beta-zeolite is used as zeolitic catalyst. It is stated, inter alia, that the boron beta-zeolites can be shaped together with a binder to form extrudates or pellets. After shaping, the extrudates or compacts are dried and calcined, with the calcination also being able to be carried out directly in the amination reactor. Further mention is made of various measures for increasing the selectivity, the operating life and the number of possible regenerations, and application of metals from solutions is also discussed. In this case, drying can be followed by repeated calcination.

Calcination in the reactor gives no activity advantage over calcination outside the reactor. In addition, the uncalcined catalyst is soft and would therefore disintegrate into dust on introduction into a reactor, e.g. a tube reactor. The extruded catalysts become hard only as a result of calcination.

None of the documents describes achievement of an increase in the hydroamination activity of calcined zeolitic catalysts which have not been deactivated by a hydroamination.

It is an object of the present invention to provide a method of increasing the hydroamination activity of calcined zeolitic catalysts which have not been deactivated by a hydroamination, and also a corresponding process for preparing alkylamines by reacting olefins with ammonia, primary or secondary amines under hydroaminating conditions over a calcined zeolitic catalyst having an increased activity. Furthermore, a corresponding catalyst having increased activity is to be provided.

We have found that this object is achieved by a process for preparing alkylamines by reacting olefins with ammonia, primary or secondary amines under hydroaminating conditions over a calcined zeolitic catalyst, wherein the calcined zeolitic catalyst is thermally activated at from 100 to 550° C. in a gaseous stream of air, nitrogen, other inert gases or mixtures thereof not more than 24 hours before commencement of the reaction.

The object is also achieved by a method of increasing the hydroamination activity of calcined zeolitic catalysts which have not been deactivated by a hydroamination by thermal treatment of the calcined zeolitic catalysts at from 100 to 550° C. in a gaseous stream of air, nitrogen, other inert gases or mixtures thereof.

According to the present invention, it has been found that thermal activation of zeolitic catalysts immediately before use enables their activity to be increased. In particular, this effect also occurs in the case of fresh catalysts which have not been used in the reaction but have been stored for relatively long periods of time after production/calcination. It has been observed that zeolitic catalysts suffer a significant reduction in activity within a few days after their production/calcination. The method of the present invention not only allows the initial activity of the catalysts before storage to be restored but also makes it possible to increase the activity further.

In the method of increasing the hydroamination activity, the thermal treatment is preferably carried out not more than 24 hours before commencement of a hydroamination in which the zeolitic catalyst is used. In the process for preparing alkylamines, the calcined zeolitic catalyst is likewise thermally activated not more than 24 hours before commencement of the reaction.

The calcined zeolitic catalyst is preferably thermally activated not more than 6 hours, particularly preferably not more than 2 hours, in particular immediately, before commencement of the reaction. The expression "not more than 24 hours before commencement of the reaction" refers to the time interval between the end of thermal activation and the commencement of the reaction in the hydroamination. In the particularly preferred case, the thermal activation is followed immediately by the reaction. This can be achieved particularly advantageously when the thermal treatment is carried out in the amination reactor itself. In this case, the catalyst does not firstly have to be cooled after the thermal activation and transferred to an amination reactor, but can instead remain in the amination reactor. The gaseous stream of air, nitrogen, other inert gases or mixtures thereof used for the thermal activation can be replaced by streams of ammonia, primary or secondary amines and olefins so that the thermal activation is followed immediately by the reaction in the hydroamination. However, brief cooling of the catalyst is not critical. The shorter the time interval between thermal activation and commencement of the reaction, the greater the activity of the calcined zeolitic catalyst.

The thermal activation is carried out at from 100 to 550° C., preferably from 150 to 525° C., in particular from 200 to 500° C. The thermal activation is carried out in a gaseous stream of air, nitrogen, other inert gases or mixtures thereof. Preference is given to using air, nitrogen or argon, in particular air, nitrogen or air/nitrogen mixtures. The activation is usually carried out at the pressure of the system or ambient pressure. However, reduced or increased pressure can also be employed. A suitable pressure range is from 0.5 to 100 bar, particularly preferably from 1 to 50 bar.

The thermal activation is preferably carried out for a period of from 3 to 50 hours, particularly preferably from 5 to 40 hours, in particular from 10 to 25 hours. The activation time can be chosen as a function of the temperature and storage state of the zeolitic catalyst and the practical requirements in each case.

The thermal treatment can be carried out outside the amination reactor, for example in a rotary tube furnace, a belt calciner or a tray furnace. However, the activation is preferably carried out directly in the amination reactor. For this purpose, the preheated gas stream instead of the olefin/ ammonium mixture is passed through the catalyst bed. The catalyst is particularly preferably present as a fixed bed.

A distinction is made between the thermal activation according to the present invention and the actual calcination of the zeolitic catalyst. The actual calcination is preferably carried out in a rotary tube furnace, since a temperature in the range from 400 to 560° C. as is necessary for the calcination can be achieved significantly more readily in a rotary tube furnace that in a tube reactor. Tube reactors are usually designed for reaction temperatures in the range from 230 to 320° C. The by-products such as water, carbon monoxide, carbon dioxide and oxides of nitrogen formed in the calcination also interfere in a subsequent amination reaction and would have to be removed from an amination reactor at not inconsiderable cost.

Calcined zeolitic catalysts are used in the process of the present invention. This means that the active composition of the catalysts is made up of zeolites. Zeolitic catalysts usually further comprise binders which are necessary for producing shaped catalyst bodies. In the production of the shaped catalyst bodies from appropriate molding compositions, it is usual for drying to be followed by calcination in order to obtain the final catalyst.

The step which concludes production of the shaped catalyst bodies is calcination. This generally requires a temperature of above 400° C. to harden the binder material. The maximum temperature is limited by the stability of the zeolite which loses its crystallinity at temperatures above 550° C. On an industrial scale, the calcination is carried out in a rotary tube furnace at from 400 to 560° C. and a residence time of from 2 to 4 hours. In the laboratory, it is usual to employ a chamber furnace and carry out the calcination at from 480 to 520° C. for a period of from 2 to 32 hours.

Suitable catalysts for the hydroamination of olefins by means of ammonia and/or a primary amine are zeolites, in particular faujasites such as X-, Y- and USY-zeolite, erionite, chabazite, mordenite, offretite, clinoptiolite, pentasils such as ZSM-5 and ZBM-10, ZSM-11, ZSM-12, MCM-22, MCM-41, MCM48, MCM-49, MCM-56, EMT, SSZ-26, SSZ-33, SSZ-37, CIT-1, PSH-3, NU-85, beta and also the boron-containing forms, for example ZBM-11, H-boron-ZSM-5, H-boron-beta, H-boron-ZSM-11, and also the gallium- or titanium-containing forms. They have a large number of catalytically active centers combined with a high surface area.

The zeolites described differ in the type and manner of the after-treatment after their preparation (for example thermal treatment, dealumination, acid treatment, metal ion exchange, etc.).

Examples of suitable zeolites may be found in U.S. Pat. Nos. 4,375,002, 4,536,602, EP-A 305 564, EP-A 101 921 and DE-A 42 06 992.

The zeolites known from EP-A 133 938, EP-A 431 451 and EP-A 132 736, which are boron, gallium, aluminum and iron silicate zeolites which may also be doped as described with alkali metals, alkaline earth metals and transition metals, are also suitable.

Further examples of suitable zeolites are the beta-zeolites known from CA-A 2 092 964, which are defined as crystalline alumino silicates having a specified composition and a pore size of more than 5 Å.

Preference is given to using metal- or halogen-modified beta-zeolites, as described, for example, in DE-A 195 30 177.

Zeolite catalysts of the pentasil type having an $SiO_2/Al_2O_3$ molar ratio of greater than or equal to 10, as are disclosed in EP-A 132 736, are also particularly useful.

Aluminum phosphates and silicoaluminophosphates include crystalline systems having zeolite structures or zeolite-like structures, for example SAPO-37, $AlPO_4$-5, SAPO-5, as described in DE-A 196 01 409, and also amorphous systems as described, for example, in DE-A 44 31 093. They generally have the formula $Al_2O_3*P_2O_5*xSiO_2$.

The catalysts can be used in the form of powder or preferably in the form of shaped bodies such as extrudates, pellets or crushed material. For the purpose of shaping, from 2 to 60% by weight, (based on the composition to be shaped) of binders can be added. Suitable binders include various aluminum oxides, preferably boehmite, amorphous aluminosilicates having a molar $SiO_2/Al_2O_3$ ratio of from 25:75 to 95:5, silicon dioxide, preferably finely divided $SiO_2$, for example silica sols, mixtures of finely divided $SiO_2$ and finely divided $Al_2O_3$, finely divided $TiO_2$ and also clays.

After shaping, the extrudates or compacts are advantageously dried at from 80 to 150° C. for from 2 to 16 hours, for example at 110° C./16 hours, and calcined at from 300 to 500° C. for from 2 to 16 hours. Like the activation, the calcination can also be carried out directly in the hydroamination reactor.

The catalysts are generally used in the H form. However, various modifications can also be made to the catalysts to increase the selectivity, the operating life and the number of possible catalyst regenerations.

One way of modifying the catalysts is to ion-exchange or dope the unshaped catalysts with alkali metals such as Na and K, alkaline earth metals such as Ca, Mg, heavy metals such as Tl, transition metals such as Mn, Fe, Mo, Cu, Zn, Cr, noble metals and/or rare earth metals such as La, Ce or Y.

In an advantageous catalyst embodiment, the shaped catalysts are placed in a flow tube and, for example, a halide, an acetate, an oxalate, a citrate or a nitrate of the above-described metals in dissolved form is passed over them at from 20 to 100° C. Such ion exchange can, for example, be carried out on the hydrogen, ammonium or alkali metal form of the catalysts.

Another possible way of applying the metals to the catalysts is to impregnate the zeolitic material with, for example, a halide, acetate, oxalate, citrate, nitrate or oxide of the above-described metals in aqueous or alcoholic solution.

Both ion exchange and impregnation can be followed by drying and, if desired, repeated calcination. In the case of metal-doped catalysts, after-treatment with hydrogen and/or with water vapor can be advantageous.

A further possible way of modifying the catalyst is to subject the heterogeneous catalytic material, shaped or unshaped, to treatment with acids such as hydrochloric acid (HCl), hydrofluoric acid (HF), phosphoric acid ($H_3PO_4$), sulfuric acid ($H_2SO_4$), oxalic acid ($HO_2C$—$CO_2H$) or mixtures thereof.

In a preferred embodiment, the catalyst powder is treated with hydrofluoric acid (from 0.001 to 2 molar, preferably from 0.05 to 0.5 molar) for from 1 to 3 hours under reflux prior to shaping. After the powder has been filtered off and washed, it is generally dried at from 100 to 160° C. and calcined at from 400 to 550° C.

In a further particular embodiment, the heterogeneous catalysts are treated with HCl after shaping together with binder. Here, the heterogeneous catalyst is generally treated with a 3–25% strength, in particular a 12–20% strength, hydrochloric acid at from 60 to 80° C. for from 1 to 3 hours, subsequently washed, dried at from 100 to 160° C. and calcined at from 400 to 550° C.

Another possible way of modifying the catalyst is exchange with ammonium salts, for example $NH_4Cl$, or with monoamines, diamines or polyamines. Here, the heterogeneous catalyst which has been shaped together with binders is generally exchanged continuously at from 60 to 80° C. by means of 10–25% strength, preferably about 20% strength, $NH_4Cl$ solution in a weight ratio of heterogeneous catalyst to ammonium chloride solution of 1:15 for 2 hours and then dried at from 100 to 120° C.

A further modification which can be carried out on aluminum-containing catalyst is dealumination in which part of the aluminum atoms is replaced by silicon, or the aluminum content of the catalysts is reduced by, for example, hydrothermal treatment. A hydrothermal dealumination is advantageously followed by extraction with acids or complexing agents to remove nonlattice aluminum formed. The replacement of aluminum by silicon can, for example, be achieved by means of $(NH_4)_2SiF_6$ or $SiCl_4$. Examples of dealuminations of Y-zeolites may be found in Corma et al., Stud. Surf. Sci. Catal. 37 (1987), pages 495 to 503.

The catalysts can be used as extrudates having diameters of, for example, from 1 to 4 mm or as pellets having diameters of, for example, from 3 to 5 mm for the hydroamination of the olefins.

The reaction of the olefin with ammonia and/or the primary amine in the presence of the inorganic solid state acid can be carried out, for example, as described in EP-A 132 736, EP-A 752 409 and EP-A 822 179.

The usual procedure is to mix ammonia and/or primary amine or, if desired, secondary amine with olefin in a molar ratio of from 1:1 to 10:1, preferably from 1:1 to 5:1, and react this mixture at from 80 to 400° C., preferably from 230 to 320° C., and a pressure of from 40 to 700 bar, preferably from 200 to 300 bar, in the gas phase or in the supercritical state in a fixed-bed reactor or in a fluidized bed.

As an alternative, the reaction can be carried out in the liquid phase at from 60 to 120° C. and a pressure of from 40 to 80 bar in a stirred vessel, a solid/liquid moving bed or a flow tube.

One embodiment of this process comprises feeding ammonia and/or the primary or secondary amine mixed with the olefin or the olefin mixture in a molar ratio of from 1:1 to 5:1 into a fixed-bed reactor in which the zeolitic catalyst is present and reacting the mixture at from 200 to 350° C., preferably from 220 to 330° C., in particular from 230 to 320° C., and a pressure of from 100 to 320 bar, preferably from 150 to 310 bar, in particular from 200 to 300 bar, in the gas phase or in the supercritical state.

The position of the equilibrium and thus the conversion to the desired hydroamination product is strongly dependent on the reaction pressure selected. A higher pressure favors the addition product, but the pressure range up to 300 bar generally represents the optimum for technical and economic reasons. The selectivity of the reaction is influenced to a high degree by the temperature and also parameters such as ammonia/amine excess and catalyst. Although the reaction rate of the addition reaction increases greatly with increasing temperature, selectivity-reducing secondary reactions may be promoted at the same time. In addition, an increase in temperature is usually not advantageous from a thermodynamic point of view. The position of the temperature optimum in respect of conversion and selectivity is dependent on the constitution of the olefin, of the primary amine used and of the catalyst and is usually in the range from 220 to 320° C.

In the process of the present invention, ammonia, primary or secondary amines are used as starting materials. The primary or secondary amines preferably have $C_{1-20}$-alkyl radicals, particularly preferably $C_{1-6}$-alkyl radicals, in particular methyl radicals or ethyl radicals.

As olefins, preference is given to using $C_{2-20}$-olefins which are aliphatic. They can be linear or branched in this case. $C_{2-12}$-olefins, in particular $C_{2-6}$-olefins, are preferably used. Examples of suitable olefins are ethene, propene, butene, isobutene and also 1,3-butadiene.

Apart from ammonia, very particularly preferred amines are monomethylamine, dimethylamine, monoethylamine, diethylamine, n-butylamine, isopropylamine, diisopropylamine and di-n-butylamine.

Hydroamination products obtained from ethene and ammonia are monoethylamine, diethylamine and/or triethylamine, from ethene and monoethylamine: diethylamine and/or triethylamine, from isobutene and ammonia: tert-butylamine, from 1,3-butadiene and ammonia: 1-amino-3-butene and/or 2-amino-3-butene, from 1,3-butadiene and n-butylamine: (2-butenyl)-n-butylamine and/or (3-butenyl)-n-butylamine, and from propene and isopropylamine: diisopropylamine.

The reaction of the olefin with the ammonia and/or the amine can be carried out as described in the abovementioned literature. The reaction can be carried out continuously, batchwise or in a semibatch mode.

In a batch process, the catalyst is preferably placed together with the amine in a reaction vessel. After the reaction temperature has been reached, the vessel is pressurized with the olefins. After the pressure has dropped, the product or product mixture is distilled off. Excess olefin and unreacted amine can be recirculated.

In a batch process, the catalyst can be discharged together with the product mixture from the bottom of the reactor and worked up separately. The reaction can be carried out in a stirred vessel.

Suitable batch and continuous processes are described in WO 02/00597 and in the literature cited above. Particular preference is given to using the zeolites as shaped bodies, with the reaction of the olefin with ammonia being carried out at from 200 to 300° C. and pressures of from 200 to 300 bar.

The catalysts obtained by the novel method of increasing the hydroamination activity of calcined zeolitic catalysts display an increased activity compared to nonactivated catalysts, and this leads to an increased product yield. The invention therefore also provides the catalysts obtainable by the activation method.

The catalysts used in the process of the present invention have preferably not been used in a hydroamination prior to thermal activation. They are thus fresh catalysts which have only been stored prior to thermal activation but have not been present in a reaction. In this way, the catalysts used in the process of the present invention differ from, in particular, the catalysts which have been recalcined according to the prior art.

The invention is illustrated by the following examples.

The examples relate to the synthesis of tert-butylamine (TBA) from isobutene and ammonia over boron beta-zeolite catalysts. The preparation of the boron beta-zeolites and the shaping of these were carried out by methods analogous to those described in EP 844 991 using boehmite as binder. The amount of binder was selected so that the finished, calcined catalyst contains 26% of $Al_2O_3$.

The performance tests were carried out in a continuously operated pilot plant. An isobutene/ammonium mixture (molar ratio 1:1.5) is passed through 10 g of catalyst as curshed material (1–1.6 mm) in a tube reactor (internal diameter: 8 mm). The temperature is 270° C., the pressure is 280 bar and the space velocity is 2.6 g (isobutene)/g (cat.)h.

EXAMPLE 1

Ex-situ Regeneration

Samples were taken from a freshly prepared batch of boron beta catalyst after various times (1 day, 6 days, 51 days) and tested in the pilot plant. The remainder was, after 58 days, activated at 500° C. in the presence of air in a furnace for 16 hours and immediately after cooling was installed in the reactor. It can be seen that the TBA (tert-butylamine) yield decreases with increasing storage, but the after-calcined catalyst still exceeds the activity of the catalyst which is only one day old.

| Storage | TBA yield |
|---|---|
| 1 d | 15.0 mol % |
| 6 d | 13.9 mol % |
| 51 d | 13.2 mol % |
| 58 d, after-calcined before installation | 15.5 mol % |

EXAMPLE 2

Ex-situ Regeneration

A freshly prepared batch of boron beta-zeolite catalyst was stored for 3 days and then tested in the pilot plant. Further catalyst from the same batch was installed after 21 days, but nitrogen was passed through it at 300° C. for 22 hours before commencement of the reaction. The catalyst which had been activated in this way displayed a significantly higher TBA yield than the untreated catalyst.

| Storage | TBA yield |
|---|---|
| 3 d | 14.3 mol % |
| 21 d, flushed with $N_2$ at 300° C. in the reactor | 17.2 mol % |

EXAMPLE 3

In-situ Regeneration

A stored catalyst was installed in the reactor of the pilot plant and displayed an activity of 15.4 mol % of TBA. The supply of feed was then switched off and nitrogen was passed through the catalyst in the reactor at 300° C. for 22 hours. When the reactor was started up again, an increase in activity to 16.2 mol % of TBA was found.

We claim:

1. A process for preparing alkylamines by reaction of olefins with ammonia, primary or secondary amines under hydroaminating conditions over a calcined zeolitic catalyst, having increased activity when used within 24 hours of thermal activation at from 100° C. to 550° C. in a gaseous stream of air, nitrogen, other inert gases or mixtures thereof to provide an improved yield of alkylamines.

2. A process as claimed in claim 1, wherein the calcined zeolitic catalyst is thermally activated not more than 6 hours before commencement of the reaction.

3. A process as claimed in claim 1, wherein the thermal activation is carried out in the amination reactor.

4. A process as claimed in claim 1, wherein the calcined zeolitic catalyst has not been deactivated by a hydroamination prior to the thermal activation.

5. A process as claimed in claim 1, wherein the zeolitic catalyst is selected from among faujasites, erionite, chabazite, mordenite, offretite, clinoptiolite, pentasils, beta-zeolites and boron-containing gallium-containing or titanium-containing forms thereof and also mixtures thereof.

6. A method of increasing the hydroamination activity of calcined zeolitic catalysts which have not been deactivated by a hydroamination by thermal treatment of the calcined zeolitic catalysts at from 100 to 550° C. in a gaseous stream of air, nitrogen, other inert gases or mixtures thereof.

7. A method as claimed in claim 6, wherein the calcined zeolitic catalyst has never been in a hydroamination prior to the thermal activation.

8. A process as claimed in claim 1, wherein the calcined zeolitic catalyst is thermally activated immediately before commencement of the reaction.

9. The process of claim 1, wherein the thermal activation continues for a time from about 3 hours to about 50 hours.

10. The process of claim 9, wherein the thermal activation continues for a time from about 10 hours to about 25 hours.

11. The process of claim 1, wherein the thermal activation proceeds at a pressure from about 0.5 bar to about 100 bar.

12. The process of claim 11, wherein the thermal activation proceeds at a pressure from about 1.0 bar to about 50 bar.

13. The process of claim 1, wherein the improved yield of alkylamines is from about 0.5 mole percent to about 3.0 mole percent.

* * * * *